(12) United States Patent
Lopes et al.

(10) Patent No.: US 7,674,398 B2
(45) Date of Patent: Mar. 9, 2010

(54) SUBSTITUTED CUMARINES, PROCESS FOR THE PRODUCTION OF SAID CUMARINES AND COMPOSITION CONTAINING SAID CUMARINES

(75) Inventors: Claudio Cerqueira Lopes, Rio de Janeiro (BR); Rosangela Sabattini Capella Lopes, Rio de Janeiro (BR); Jari Cardoso Norbega, Rio de Janeiro (BR); Glaucia Slans Alves Barbosa, Rio de Janeiro (BR); Maicon Guerra, Niteroi-Rio de Janeiro (BR); Jose Roque Mota Carvalho, Bahia (BR)

(73) Assignee: Universidade Federal do Rio de Janerio UFRJ, Rio de Janeiro (BR)

( * ) Notice: Subject to any disclaimer, the term of this patent is extended or adjusted under 35 U.S.C. 154(b) by 145 days.

(21) Appl. No.: 11/574,845

(22) PCT Filed: Sep. 20, 2005

(86) PCT No.: PCT/BR2005/000188

§ 371 (c)(1),
(2), (4) Date: Mar. 7, 2007

(87) PCT Pub. No.: WO2006/032120

PCT Pub. Date: Mar. 30, 2006

(65) Prior Publication Data

US 2008/0011985 A1    Jan. 17, 2008

(30) Foreign Application Priority Data

Sep. 20, 2004 (BR) .................. 0404130

(51) Int. Cl.
*C07D 311/08* (2006.01)
(52) U.S. Cl. ............... 252/301.16; 252/301.32; 549/285; 549/289; 549/290
(58) Field of Classification Search ......... 549/285, 549/289, 290; 252/301.16, 301.32
See application file for complete search history.

(56) References Cited

U.S. PATENT DOCUMENTS 3,514,471 A * 5/1970 Kotoyori et al. ............ 549/288
3,636,004 A * 1/1972 Bode et al. ............... 548/266.4
5,755,860 A * 5/1998 Zhu ....................... 106/31.15

* cited by examiner

*Primary Examiner*—C. Melissa Koslow
(74) *Attorney, Agent, or Firm*—Smith, Gambrell & Russell

(57) ABSTRACT

Present invention refers to substituted cumarines that are capable to emit fluorescent light when illuminated by wave lengths within ultraviolet range. Present invention also refers to process of production of said substituted cumarines, well as provides compositions containing said substituted cumarines, especially compositions containing said cumarines and volatile solvents and/or adjuvants. Said compositions can be used in objects of great value for its owner, in view of facilitating the identification of such objects.

2 Claims, No Drawings

SUBSTITUTED CUMARINES, PROCESS FOR THE PRODUCTION OF SAID CUMARINES AND COMPOSITION CONTAINING SAID CUMARINES

FIELD OF INVENTION

The present invention discloses substituted coumarins, especially 3-alkyl and 3-aryl coumarins. Such coumarins have the capability to emit fluorescent light when illuminated by a wave length comprised in the ultraviolet range.

The present invention also discloses a process for the production of said substituted coumarins, especially, a reaction of a 2-hydroxy-benzaldehyde and a carboxylic acid with more than 3 carbon atoms or phenylacetic acid and derived thereof in a non-aqueous solvent, in the presence of TEA and an acyl chloride.

In addition, the present invention discloses compositions containing said substituted coumarins and volatile solvents and/or adjuvants. Said compositions can be used in objects of great value for its proprietary, being an auxiliary agent for the protection of public and private patrimony.

BACKGROUND OF THE INVENTION

For a long time, robberies, burglaries and falsifications in goods of public or private patrimony, either small or great in size (like computers, laboratory equipments, etc), disturb the society.

There are many cases of people related to universities or even common people that had their objects burglarized or falsified in a way that a layperson would not be able to check such irregularities, otherwise by incorrect running of said object.

In an attempt to minimize or solve these problems, measures involving the development of technologies for preventing burglaries and falsifications have been created along the years. However, up to the present date, no 3-aryl coumarins synthesis have been reached, as the one which will be described.

From the state of the art, there are many documents that describe compositions that are made visible through the use of infrared or ultraviolet light or that is made visible by a thermochromatic method, marking methods to protect objects, authentication of documents using a natural light-transparent adhesive, etc.

To illustrate the above mentioned, the following documents are disclosed:

The United States patent application US 2004/069184 by Neil S. Fox and Christopher P. Finke, filed on Sep. 17, 2003, discloses a marking composition that includes a base and colorant pigments for inserting a invisible marking temporarily with the use of UV light on the desired surface. However, the pigment of this invention is a dispersion of a melamine-toluenesulfonamide-formaldehyde polymer.

The U.S. Pat. No. 6,409,218 of Volkswagen AG, filed on 15 Jun. 2, 2000, discloses marks that become invisible through UV dye, which may be visualized by UV light that are used to protect equipments of robberies and burglaries.

The European patent EP 626 660, of Pitney Bowes Inc., filed on May 20, 1994, discloses a document authentication system, in which a transparent identification stamp is used and becomes visible only when an infrared light is applied over it.

The U.S. Pat. No. 6,513,921 of Hewlett-Packard Company, filed on May 12, 2000 discloses a printing method of an invisible image over a substrate, which becomes visible when submitted to fluorescence, wherein such dye is composed of a ftalocianine and a compound capable of absorbing UV radiation selected from the group that consists of stilbene, pyrazoline, coumarin, carbostiryl or pirene. This document does not detail coumarins, citing only as example 7-diethylamino-4-methylcoumarin, 7-hydroxy-4-methylcoumarin e 3-(2-benzimidazolyl)-7-(diethylamine) coumarin.

Regarding prior art from Brazil, it can be described, also as illustrative examples, some documents that comment on this subject, such as:

The Brazilian utility Model MU 7202088, of Vanice Zanoni et al., filed on Dec. 1, 1992, discloses thermochromatic dyes formed by pigments that might be added to many coloration processes that become visible on presence of sun light and UV rays, and invisible in the absence of said rays.

The Brazilian patent PI 9609576 of Lawson Mardon USA Inc. et al., filed on Jul. 8, 1996, discloses a labeling system in which the label includes a trigger mark formed by luminophore light, i.e., contain an agent of fluorescent optical track that reflect as visible light directed to UV light.

The Brazilian patent application PI 9803076 patent of Osvaldo Marchesi, filed on Aug. 21, 1998, discloses a chromatic identification system that occurs through UV light and in which important information is printed with invisible polymer-based dye, that chromatically reacts under incidence of UV light emitted by a lamp.

Still regarding documents that are already known in state of the art, synthesis process of compounds from coumarin group were already disclosed. However, the main function of these compounds is the antifungal, antimicrobial or antitumoral action. The document CN1450062 of Shanghai Inst Organic Chem filed on Oct. 22, 2003, discloses chiral coumarins with substitution on position 4, while the document EP 816 353 of Etichka Ind Dionichko Drushtvo discloses coumarins where position 3 is only substituted by N, O or H.

However, as it can be concluded from the above reading, there is no evidence in the state of the art concerning the application of the compounds of the coumarins group, which the main action is the provision of fluorescence in the UV either in low and high wave length.

Therefore, the composition developed by the invention, not only the goods and/or value objects owners will be benefited, but also the investigative police will be able to partake of its benefits, as the invention may help the elucidation of kidnapping, extortion, homicides, larceny, robberies, burglaries, etc.

SUMMARY OF THE INVENTION

It is an objective of the present invention to provide substituted coumarin compounds. Specifically, said coumarins are substituted in position 3, being preferred compounds of the invention 3-alkylcoumarins and/or 3-arylcoumarins. More specifically, said coumarins have general formula (I):

$$(R_1)n \text{—[coumarin ring]—} R_2 \quad (I)$$

where:

n is an integer chosen from 1, 2, 3 or 4;

$R_1$ corresponds to C1-C4 alkyl, C1-C4 alkenyl, C1-C4 alkinyl, C1-C4 alcoxyls, aryl, C1-C4 acyl, halides, cyano, C1-C4 dialkylamines, methylenedioxy, sulfonamides, sulfoxamides, and mixtures thereof, where each of these radicals can be optionally substituted;

$R_2$ corresponds to C1-C4 alkyl, C1-C4 alkenyl, C1-C4 alkinyl, C1-C4 alcoxyls, aryl, C1-C4 acyl, halides, cyano, C1-C4 dialkylamines, methylenedioxy, sulfonamides, sulfoxamides, and mixtures thereof, where each of these radicals can be optionally substituted.

A further object of the present invention is a process for the production of these substituted coumarins. Specifically, such process comprises the reaction steps of an aldehyde with a carboxylic acid. More specifically, such preferential process of this invention consists of an aldehyde reaction, where said aldehyde has the general formula (II),

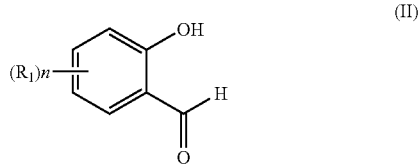

where:

n is an integer chosen from 1, 2, 3 or 4;

$R_1$ is an C1-C4 alkyl, C1-C4 alkenyl, C1-C4 alkinyl, C1-C4 alcoxyls, aryl, C1-C4 acyl, halides, cyano, C1-C4 dialkylamines, methylenedioxy, sulfonamides, sulfoxamides, and mixtures thereof, where each of these radicals can be optionally substituted;

with carboxylic acids of general formula (III)

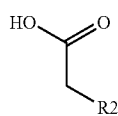

where:

$R_2$ is an C1-C4 alkyl, C1-C4 alkenyl, C1-C4 alkinyl, C1-C4 alcoxyls, aryl, C1-C4 acyl, halides, cyano, C1-C4 dialkylamines, sulfonamides, sulfoxamides, and mixture thereof, where each of these radicals can be optionally substituted; especially, the process for the production occurs in the presence of a non-aqueous solvent, TEA and a acyl chloride.

A further object of the present invention is a composition containing substituted coumarins, especially coumarins which general formula (I) is:

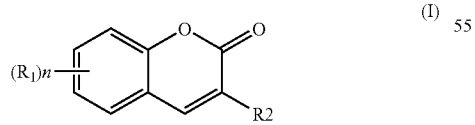

where:

n is an integer chosen from 1, 2, 3 or 4;

$R_1$ corresponds to C1-C4 alkyl, C1-C4 alkenyl, C1-C4 alkinyl, C1-C4 alcoxyls, aryl, C1-C4 acyl, halides, cyano, C1-C4 dialkylamines, methylenedioxy, sulfonamides, sulfoxamides, and mixtures thereof, where each of these radicals can be optionally substituted;

$R_2$ corresponds to C1-C4 alkyl, C1-C4 alkenyl, C1-C4 alkinyl, C1-C4 alcoxyls, aryl, C1-C4 acyl, halides, cyano, C1-C4 dialkylamines, methylenedioxy, sulfonamides, sulfoxamides, and mixtures thereof, where each of these radicals can be optionally substituted.

More specifically, such composition comprises substituted coumarins and suitable solvents/adjuvants, especially volatile solvents/adjuvants.

DETAILED DESCRIPTION OF THE INVENTION

For means of the present invention, it is considered as "ultraviolet radiation wave lengths", wave lengths which varies from 380 nm to 10 nm; it is considered as "luminescence" the capability of a substance of emitting light when excited. The luminescence may be subdivided in fluorescence and phosphorescence; it is considered as "fluorescence" the capability of a substance emitting light in a wave length located in the region of visible light when excited by other electromagnetic radiation forms, for example, UV rays, infrared, X-rays, etc.

The examples shown herein shall not be faced in a restrictive form, being only a embodiment form of the invention.

Substituted coumarins of the present invention follow the general formula (I):

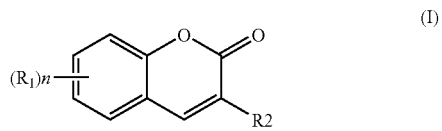

where:

n is an integer chosen from 1, 2, 3 or 4;

$R_1$ corresponds to C1-C4 alkyl, C1-C4 alkenyl, C1-C4 alkinyl, C1-C4 alcoxyls, aryl, C1-C4 acyl, halides, cyano, C1-C4 dialkylamines, methylenedioxy, sulfonamides, sulfoxamides, and mixtures thereof, where each of these radicals can be optionally substituted;

$R_2$ corresponds to C1-C4 alkyl, C1-C4 alkenyl, C1-C4 alkinyl, C1-C4 alcoxyls, aryl, C1-C4 acyl, halides, cyano, C1-C4 dialkylamines, methylenedioxy, sulfonamides, sulfoxamides, and mixtures thereof, where each of these radicals can be optionally substituted.

Substituted coumarins of the present invention might be prepared by several techniques and synthetic routes. A preferred process of his invention consists of reacting an aldehyde of general formula (II),

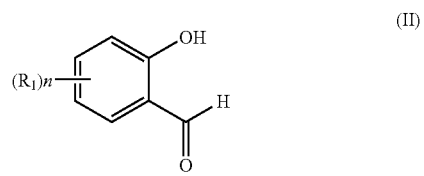

where:

n is an integer chosen from 1, 2, 3 or 4;

$R_1$ is an C1-C4 alkyl, C1-C4 alkenyl, C1-C4 alkinyl, C1-C4 alcoxyls, aryl, C1-C4 acyl, halides, cyano, C1-C4 dialkylamines, methylenedioxy, sulfonamides, sulfoxamides, and mixtures thereof, where each of these radicals can be optionally substituted;

with carboxylic acids of general formula (III)

where:
R$_2$ is an C1-C4 alkyl, C1-C4 alkenyl, C1-C4 alkinyl, C1-C4 alcoxyls, aryl, C1-C4 acyl, halides, cyano, C1-C4 dialkylamines, sulfonamides, sulfoxamides, and mixture thereof, where each of these radicals can be optionally substituted;

More specifically, coumarins of the present invention might be prepared according the following scheme:

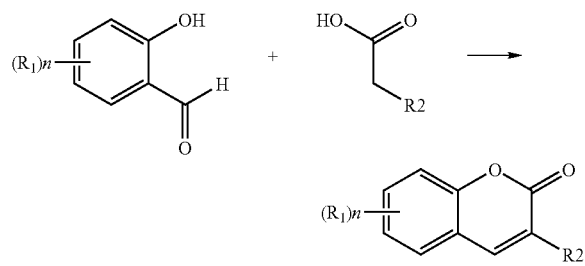

Said reaction is performed in the presence of: (i) an aprotic polar solvent, since the utilization of said solvent facilitates reverse reaction of the hydrogen abstraction in the alpha position related to the carbonyl; (ii) an alcalinizing agent, carbanion-species former, the nucleophile responsible for the development of the intramolecular aldolic condensation; and (iii) dehydrating agent, water elimination promoter with subsequent aromatization and formation of the desired coumarin heterocyclic system, this substance being the N,N-diethylamine hydrochloride, which is formed in the reactional medium. The temperature at the beginning of the reaction must be kept under the water freezing point, in order to avoid undesirable condensations, conducing the polymeric products formation, significantly decreasing the process global yield and forming the appropriated mixed anhydride, the key intermediary of the 3-alkyl and 3-aryl-coumarins synthesis process.

The global reaction fundamentally comprises the following steps: a) formation of a mixed anhydride; and b) aldolic condensation reaction. Other solvents may be used on this type of transformation, such as: dichloromethane, 1,2-dichloromethane, chloroform, ethyl ether and N,N-dimethylformamide. However, very poor yields were obtained on this trials. Using the tetrahydrofuran, excellent yields to the same chemical transformations were obtained.

The triethylamine is a base having two distinct functions on this process: (1) reacts with the suitable carboxylic acid in the first step forming the corresponding carboxylate, which will attack the carbonyl of the pivaloyl chloride generating the mixed anhydride with the suitable function to the acylation reaction in the oxygen atom on the position 2 of the 2-hydroxibenzaldehyde, used to build the A ring of the 3-aryl cumarine system; (2) captures proton of the alpha position related to the carbonyl of the O-acylated intermediary, obtained via reaction with the mixed anhydride, generating a carbanion that will act as nucleophile towards the carbonyl of the aromatic aldehyde forming the desired heteroaromatic system through intramolecular aldolic condensation.

The pivaloyl chloride is the chosen reagent for the promotion of the acylation reactions using carboxylic acids as acylating agents towards substrates rich in electrons. In this case, the phenolate formed by proton capture with TEA is the suitable nucleophile to react with the carbonyl from the carboxylic acid, employed as acylating agent and further to change the substitution pattern on position 3 of the coumarin system. The attack is regioselective in one of the carbonyls, since observing formed mixed anhydride structure, the carbonyl adjacent to the tert-butyl group is the most esterically blocked, enhancing the phenolat attack in the appropriate acylating agent, which on this case, in the carbonyls of the propionic or butyric acid or phenylacetic acid and derivatives thereof.

The following example illustrates a possible production process of the substituted coumarins (all based on volume):

In a 125 ml volumetric flask, 1.23 g (MM=136:. 23 g= 0.009044 mol or 9.0 mmols) of phenylacetic acid and 10 ml of dry THF (tetrahydrifuran) were added.

The suspension formed was conducted at temperature of –15° C.

To this was added 2.5 ml of dry TEA (triethylamine) (d=0.726; 1.82 g; MM=101:. 1.82 g=0.018019 mol or 10.02 mmols).

The mixture was agitated for 10 minutes, and thus, at the same temperature, 1.1 ml of pivaloyl chloride (d=0.979; 1.08 g; MM=120.5:.1.08 g=0.00896 mol or 8.96 mmols) was added.

The reaction was kept at temperature of –15° C. for 30 minutes.

After this, 5 ml of a THF solution and 1.0 g (MM= 122:. 1.0 g=0.0081967 mol or 8.2 mmoles) of salicylaldehyde were added at the same time.

The mixture was then refluxed by 24 hours.

Having the coumarins, a composition containing such substances can be prepared, wherein said composition is ideal for marking and identifying any desired object.

The composition comprises the following substances:
substituted coumarins according general formula (I)
volatile organic solvent
non-volatile organic solvent The composition contains preferably from 1% w/v to 10% w/v of substituted coumarin and the ratio of volatile solvent to non-volatile solvent varies from 1:5 to 5:1.

An illustrative example of a composition is shown below:
100 mg of substituted coumarin according to the general formula (I)
2 ml of aprotic solvent, such as DMF, dioxane, dichloromethane, 1,2-dichloroethane, THF
1 mL of pirrolidone

The invention claimed is:

1. A coumarin composition comprising the following substances:
(i) substituted coumarins according to general formula (I):

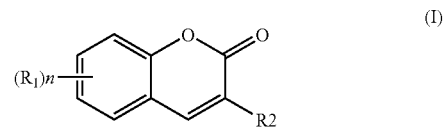

where:
n is an integer chosen from 1, 2, 3 or 4;
R$_1$ corresponds to C1-C4 alkyl, C1-C4 alkenyl, C1-C4 alkinyl, C1-C4 alcoxyls, aryl, C1-C4 acyl, halides, cyano, C1-C4 dialkylamines, methylenedioxy, sulfonamides, sulfoxamides, and mixtures thereof, where each of these radicals can be optionally substituted;

$R_2$ corresponds to C1-C4 alkyl, C1-C4 alkenyl, C1-C4 alkinyl, C1-C4 alcoxyls, aryl, C1-C4 acyl, halides, cyano, C1-C4 dialkylamines, methylenedioxy, sulfonamides, sulfoxamides, and mixtures thereof, where each of these radicals can be optionally substituted;

(ii) volatile organic solvent; and
(iii) non-volatile organic solvent.

2. The coumarin composition according to claim 1, comprising from 1% w/v to 10% w/v of the substituted coumarin according to general formula (I) and the ratio of the volatile solvent to the non-volatile solvent varies from 1:5 to 5:1.

* * * * *